US012589065B2

(12) United States Patent
Pinto et al.

(10) Patent No.: US 12,589,065 B2
(45) Date of Patent: Mar. 31, 2026

(54) HAIR CARE SYSTEM, HAIR CARE METHOD AND USE OF A HAIR CARE SYSTEM

(71) Applicant: L'OREAL, Paris (FR)

(72) Inventors: Celso Alexandre Abreu Pinto, Rio de Janeiro (BR); Ana Claudia Meda Siloto, Rio de Janeiro (BR); João Paulo Duarte Guimaraes, Rio de Janeiro (BR); Andrea Kim, Rio de Janeiro (BR); Jessica Gallafrio, Rio de Janeiro (BR); Leandro Valeriano De Carvalho, Rio de Janeiro (BR); Danielle Pantoja, Rio de Janeiro (BR)

(73) Assignee: L'OREAL, Paris (FR)

( * ) Notice: Subject to any disclaimer, the term of this patent is extended or adjusted under 35 U.S.C. 154(b) by 850 days.

(21) Appl. No.: 17/422,524

(22) PCT Filed: Jan. 17, 2019

(86) PCT No.: PCT/BR2019/050016
§ 371 (c)(1),
(2) Date: Jul. 13, 2021

(87) PCT Pub. No.: WO2020/146931
PCT Pub. Date: Jul. 23, 2020

(65) Prior Publication Data
US 2022/0096358 A1 Mar. 31, 2022

(51) Int. Cl.

| | |
|---|---|
| *A61K 8/898* | (2006.01) |
| *A61K 8/06* | (2006.01) |
| *A61K 8/34* | (2006.01) |
| *A61K 8/39* | (2006.01) |
| *A61K 8/41* | (2006.01) |

(Continued)

(52) U.S. Cl.
CPC .............. *A61K 8/898* (2013.01); *A61K 8/062* (2013.01); *A61K 8/342* (2013.01); *A61K 8/416* (2013.01); *A61K 8/44* (2013.01); *A61K 8/463* (2013.01); *A61K 8/737* (2013.01); *A61K 8/891* (2013.01);
(Continued)

(58) Field of Classification Search
None
See application file for complete search history.

(56) References Cited

U.S. PATENT DOCUMENTS

2015/0313828 A1 11/2015 Hilvert et al.
2015/0313832 A1 11/2015 Hilvert et al.
(Continued)

FOREIGN PATENT DOCUMENTS

WO 2014100970 A1 7/2014
WO 2017108824 A1 6/2017
WO 2018234444 A1 12/2018

OTHER PUBLICATIONS

International Search Report and Written Opinion issued on Oct. 10, 2019 for corresponding PCT Application No. PCT/BR2019/050016.
(Continued)

*Primary Examiner* — Kyung S Chang
(74) *Attorney, Agent, or Firm* — POLSINELLI PC

(57) ABSTRACT

The present application relates to a hair care system comprising a shampoo composition (A) and a conditioner composition (B), and optionally a mask composition (C). The invention is also related to a hair care method and the use of a hair care system.

18 Claims, 3 Drawing Sheets

(51) Int. Cl.

| | |
|---|---|
| ***A61K 8/44*** | (2006.01) |
| ***A61K 8/45*** | (2006.01) |
| ***A61K 8/46*** | (2006.01) |
| ***A61K 8/73*** | (2006.01) |
| ***A61K 8/891*** | (2006.01) |
| ***A61Q 5/02*** | (2006.01) |
| ***A61Q 5/12*** | (2006.01) |

(52) U.S. Cl.

CPC ................. *A61Q 5/02* (2013.01); *A61Q 5/12* (2013.01); *A61K 2800/884* (2013.01)

(56) References Cited

U.S. PATENT DOCUMENTS

| | | | | |
|---|---|---|---|---|
| 2015/0313833 | A1 | 11/2015 | Hilvert et al. | |
| 2019/0201315 | A1 | 7/2019 | Gevgilili et al. | |
| 2020/0268621 | A1 * | 8/2020 | Roy ......................... | A61K 8/44 |

OTHER PUBLICATIONS

Database GNPD; Mintel; "Deep-Penetrating Reconstructor," 2015 XP055522391.
MINTEL: "Hair Mask," 2006 XP002553580.

* cited by examiner

HAIR CARE SYSTEM, HAIR CARE METHOD AND USE OF A HAIR CARE SYSTEM

CROSS-REFERENCE TO RELATED APPLICATIONS

This application is a national stage application (under 35 U.S.C. § 371) of PCT/BR2019/050016, filed Jan. 17, 2019, which is incorporated herein by reference in its entirety.

FIELD OF THE INVENTION

The present application relates to a hair care system comprising a shampoo composition (A) and a conditioner composition (B), and optionally a mask composition (C). The invention is also related to a hair care method and the use of a hair care system.

BACKGROUND OF THE INVENTION

In the field of the cosmetic treatment of keratin fibers, in particular human keratin fiber, and in particular the hair, consumers desire hair care treatments that can impart moisture and reconstruct the damaged hair, which can improve the appearance of frizzy hair.

The quality and condition of hair is generally adversely affected by the action of external agents such as sunlight, wind, pollution, humidity, and chemicals in swimming pools, and also by mechanical or chemical treatments, such as brushing, combing, shampooing, dyeing, bleaching, permanent-waving and/or relaxing. Hair is thus damaged by these various factors and may over time become dry, coarse or dull, especially in fragile areas, and more particularly at the ends leading to split ends. Under such circumstances, the hair can also become less manageable, more frizzy and less disciplined, and more difficult to style or shape.

These attacks have repercussions on the quality of keratin fibers, and can in particular cause a degradation of the surface properties of keratin fibers, which become less smooth and uneven at the surface, hence they are not as easy to disentangle and have a less pleasant feel, whether dry or wet.

Although care products that address these problems already exist in the market, the hair care system of the present invention makes it possible to obtain improved results in the hair, such as better manageability, discipline, detangle, softness and clean feel, repair and texture satisfaction, frizz control or less frizziness, and less hair breakage.

SUMMARY OF THE INVENTION

The present invention is related to a hair care system comprising A) the shampoo and B) the conditioner of the present invention, and optionally C) the mask of the present invention, that makes it possible to overcome the drawbacks set out above.

When compared to the prior art, the hair care system of the present invention results in hair that is more manageable, disciplined, easier to detangle, with improved softness and clean feel, repair and texture satisfaction.

DETAILED DESCRIPTION OF THE INVENTION

Figure 1:
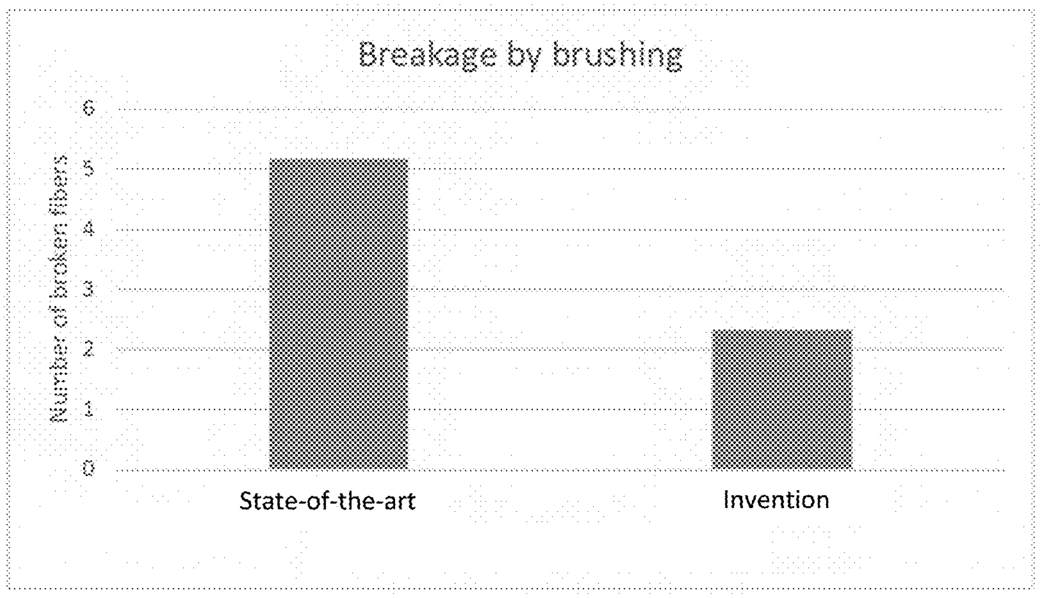
FIG. 1 shows the results obtained from an instrumental test for evaluating hair breakage in terms of number of broken fibers using a brushing machine.

A suitable hair care system of the present invention comprises:

(A) a shampoo composition, comprising:

(a) from about 5 to about 15 wt. % of at least one ethoxylated sulfate anionic surfactant having at least one degree of ethoxylation and/or its salt thereof;

(b) from about 1 to about 10 wt. % of at least one non-ethoxylated sulfate anionic surfactant and/or its salt thereof;

(c) from about 1 to about 5 wt. % of at least one amphoteric surfactant;

(d) from about 0.1 to about 3 wt. % of at least one water-soluble quaternary ammonium compound;

(e) an oil-in-water emulsion having a particle size D50 of less than 350 nm, and comprising:

a silicone mixture comprising:

(i) a polydialkylsiloxane comprising trialkylsilyl end groups, having a viscosity at 25° C. ranging from 40,000 to 100,000 mPa·s; and (ii) an aminosilicone having a viscosity at 25° C. ranging from 1,000 to 15,000 mPa·s and an amine number ranging from 2 to 10 mg of KOH per gram of aminosilicone;

a surfactant mixture comprising one or more non-ionic surfactants, said mixture having an HLB ranging from about 10 to about 16, and water;

all weights being based on the total weight of the shampoo composition and (B) a conditioner composition, comprising:

(a) from about 0.5 to about 2 wt. % of each of at least two different cationic surfactants, in a total amount of from about 1 to about 4 wt. % of cationic surfactant;

(b) from about 3 to about 5 wt. % or from about 3.5 to about 4.5 wt. % or from about 4 to about 4.5 wt. % of at least one fatty alcohol;

(c) from about 0.7 to about 3.0 wt. % of at least two silicones;

(d) water;

All weights being based on the total weight of the conditioner composition.

In a preferred embodiment, the amount of ethoxylated sulfate anionic surfactant of the shampoo composition (A) ranges from about 7 to about 11 wt. % or from about 7 to about 9 wt. % or about 7 to about 8 wt. %, based on the total weight of the composition, including ranges and sub-ranges therebetween, and is preferably selected from, but not limited to, sodium laureth sulfate, ammonium laureth sulfate, and a mixture thereof.

In a preferred embodiment, the non-ethoxylated sulfate anionic surfactant of the shampoo composition (A) ranges from about 2 to about 8 wt. % or about 3 to about 6 wt. % or about 3.5 to about 5 wt. %, based on the total weight of the composition, including ranges and sub-ranges therebetween, and is preferably selected from, but not limited to, sodium lauryl sulfate, ammonium lauryl sulfate, and a mixture thereof.

In a preferred embodiment, the total amount of ethoxylated sulfate anionic surfactant and non-ethoxylated sulfate anionic surfactant of the shampoo composition (A) ranges from about 6 to about 25 wt. % or from about 8 to about 20 wt. % or about 10 to about 18 wt. % or about 11.5 to about 15 wt. %, based on the total weight of the composition, including ranges and sub-ranges therebetween.

In a preferred embodiment, the amphoteric surfactant of the shampoo composition (A) ranges from about 1.5 to about 4 wt. % or about 2 to about 3.5 wt. % or about 2.5 to about 3.1 wt. %, based on the total weight of the composition, including ranges and sub-ranges therebetween, and is preferably selected from, but not limited to, betaines, alkyl amphoacetates, alkyl amphoproprionates, salts thereof, a mixture thereof.

The betaine may be selected from the group comprising alkyl betaines, alkyl amidopropyl betaines, alkyl sulfobetaines (sultaines), or mixtures thereof.

Preferably, the amphoteric surfactants of the shampoo composition (A) are selected from cocamidopropyl betaine, coco-betaine, or mixtures thereof.

In an embodiment, the amphoteric surfactants of the shampoo composition (A) comprise cocamidopropyl betaine and coco-betaine. Preferably, the cocamidopropyl betaine ranges from about 2 to about 4 wt. % or about 2.4 to about 3.5 wt. % or about 2.5 to about 2.8 wt. %, based on the total weight of the composition, including ranges and sub-ranges therebetween, and the coco-betaine ranges from about 0.1 to about 0.5 wt. % or about 0.15 to about 0.4 wt. % or about 0.2 to about 0.3 wt. %, based on the total weight of the composition, including ranges and sub-ranges therebetween.

In a preferred embodiment, the water-soluble quaternary ammonium compound of the shampoo composition (A) ranges from about 0.1 to about 2.5 wt. % or about 0.1 to about 2 wt. % or about 0.1 to about 1 wt. %, based on the total weight of the composition, including ranges and sub-ranges therebetween, and is preferably derived from guar gum, and is more preferably selected from guar hydroxypropyltrimonium chloride, hydroxypropyl guar hydroxypropyl trimonium chloride, and a mixture thereof.

Preferably, the viscosity of the water-soluble quaternary ammonium of the shampoo composition (A) ranges from 2.500 to 4.000 m·Pas.

In an embodiment, the silicone mixture of the shampoo composition (A) comprises one or more polydialkylsiloxanes comprising trialkylsilyl end groups of formula (I): R'3SiO(R'2SiO)pSiR'3 in which:

- R', which may be identical or different, is a monovalent hydrocarbon-based radical having from 1 to 18 carbon atoms, preferably from 1 to 6 carbon atoms, better still from 1 to 3 carbon atoms, even better still a methyl radical, and
- p is an integer ranging from 500 to 2,000, better still from 1,000 to 2,000; preferably having a viscosity ranging from 40,000 to 100,000 mPa·s at 25° C., preferably ranging from 40,000 to 70,000 mPa·s at 25° C., better still from 51 000 to 70,000 mPa·s at 25° C.

In an embodiment, the silicone mixture of the shampoo composition (A) comprises one or more aminosilicones of formula (II):

XR2Si(OSiAR)*n*(OSiR2)*m*OSiR2*X* in which:

- R, which may be identical or different, is a monovalent hydrocarbon-based radical having from 1 to 18 carbon atoms, preferably from 1 to 6 carbon atoms, better still from 1 to 3 carbon atoms, even better still a methyl radical,
- X, which may be identical or different, represents R or a hydroxyl (OH) or a C1-C6 alkoxy group; preferably X is R, that is to say a monovalent hydrocarbon-based radical having from 1 to 18 carbon atoms, preferably from 1 to 6 carbon atoms, better still from 1 to 3 carbon atoms, even better still a methyl radical,
- A is an amino radical of formula —R1-[NR2-R3-]XNR22, or the protonated form of this amino radical, with
- R1 representing a $C_1$-$C_6$ alkylene radical, preferably a $—CH_2CH_2CH_2—$ or $—CH_2CH(CH_3)CH_2—$ radical,
- R2, which may be identical or different, being a hydrogen atom or a $C_1$-$C_4$ alkyl radical, preferably a hydrogen atom,
- R3 being a $C_1$-$C_6$ alkylene radical, preferably a $—CH_2CH_2—$ radical,
- x being 0 or 1;
- m and n are integers such that m+n ranges from 50 to 1000, better still from 50 to 600;

preferably having a viscosity at 25° C. ranging from 1000 to 15 000 mPa·s, preferably from 1500 to 15 000 mPa·s, and/or an amine number ranging from 2 to 10 mg of KOH per gram of aminosilicone, preferably from 3.5 to 8 mg.

In an embodiment, the silicone mixture of the shampoo composition (A) comprises (i) one or more polydialkylsiloxanes comprising trialkylsilyl end groups, having a viscosity, at 25° C., ranging from 40 000 to 100 000 mPa·s, in an amount of from 70% to 90% by weight, preferably from 75% to 85% by weight, and (ii) one or more aminosilicones having a viscosity, at 25° C., ranging from 1000 to 15 000 mPa·s and an amine number ranging from 2 to 10 mg of KOH per gram of aminosilicone, in an amount of from 10% to 30% by weight, in particular from 15% to 25% by weight, relative to the total weight of the silicone mixture.

In an embodiment, the silicone mixture of the shampoo composition (A) comprises one or more non-ionic surfactants chosen from:

(i) (poly)oxyalkylenated, in particular (poly)ethoxylated, fatty alcohols, and in particular those of formula: $R3-(OCH_2CH_2)_cOH$ in which:
- R3 represents a linear or branched alkyl or alkenyl radical comprising 8 to 40 carbon atoms and in particular 8 to 30 carbon atoms, optionally substituted with one or more, in particular 1 to 4, hydroxyl groups; and
- c is an integer ranging from 1 to 200, in particular from 2 to 150, or even from 4 to 50 and even better still from 8 to 20;

(ii) (poly)oxyalkylenated ($C_8$-$C_{32}$)alkyl phenyl ethers, in particular comprising from 1 to 200, better still from 1 to 30 mol of ethylene oxide;

(iii) polyoxyalkylenated esters of $C_8$-$C_{32}$ fatty acids and of sorbitan, in particular polyoxyethylenated esters of $C_8$-$C_{32}$ fatty acids and of sorbitan, preferably having from 2 to 40 ethylene oxide units, better still from 2 to 20 ethylene oxide (EO) units; in particular polyoxyethylenated esters of $C_{10}$-$C_{24}$ fatty acids and of sorbitan, preferably having from 2 to 40 ethylene oxide units, better still from 2 to 20 ethylene oxide (EO) units; and (iv) polyoxyethylenated esters of $C_8$-$C_{32}$ fatty acids, preferably having from 2 to 150 ethylene oxide units; in particular polyoxyethylenated esters of $C_{10}$-$C_{24}$ fatty acids, comprising in particular 2 to 150 ethylene oxide (EO) units.

In an embodiment, the oil-in-water emulsion comprises:

the surfactant mixture in a total amount ranging from 5% to 15% by weight, in particular from 8% to 15% by weight, even better still from 10% to 12% by weight, relative to the total weight of the emulsion; and/or the non-ionic surfactant(s) in a total amount ranging from 5% to 15% by weight, in particular from 8% to 15% by weight, even better still from 10% to 12% by weight, relative to the total weight of the emulsion;

the silicone mixture in a total amount ranging from 40% to 60% by weight, in particular from 45% to 55% by weight, relative to the total weight of the emulsion; and/or the polydialkylsiloxane(s) comprising trialkylsilyl end groups, in a total amount ranging from 35% to 45% by weight, in particular from 38% to 42% by weight, relative to the total weight of the emulsion; and/or the aminosilicone(s) in a total amount ranging from 5% to 15% by weight, in particular from 8% to 12% by weight, relative to the total weight of the emulsion; and/or water in a total amount ranging from 25% to 50% by weight, in particular from 30% to 45% by weight, even better still from 35% to 42% by weight, relative to the total weight of the emulsion.

In an embodiment, the oil-in-water emulsion has a particle size D50 of between 100 and 300 nm, better still between 150 and 250 nm, or even between 160 and 200 nm.

In an embodiment, the oil-in-water emulsion is present in the shampoo composition (A) in a total amount ranging from about 0.1% to about 10% by weight, better still from about 0.2% to about 8% by weight, preferentially from about 0.5% to about 6% by weight, based on to the total weight of the composition, including ranges and sub-ranges therebetween.

In a preferred embodiment, the shampoo composition (A) of the present invention further comprises from about 0.1 to about 3 wt. % or from about 0.5 to about 2 wt. % or from about 1 to about 1.4 wt. %, based on the total weight of the composition, including ranges and sub-ranges therebetween, of at least one pearlizing agent, selected from a group of esters, preferably glycol distearate.

The shampoo composition (A) of the hair care system of the present invention may comprise additional miscellaneous ingredients or additives such as conditioning agents, humectants, preservatives, chelating agents, UV filters, pH adjusters, fragrance, pigments/colorants, and anti-dandruff/seborrheic agents.

In a preferred embodiment, the weight ratio between the at least two cationic surfactants of the conditioner composition (B) ranges from about 1:1 to about 1:4. Preferably, the weight ratio between the at least two cationic surfactants can range from be about 1:1 or 1:1.5 or 1:2 or 1:2.5 or 1:3 or 1:3.5 or can range from about 1:1.5 to about 1:3.8 or about 1:2 to about 1:3.5 or about 1:2.2 to about 1:3.2 or about 1:2.5 to about 1:3 or about 1:2.5 to about 1:2.8, including ranges and sub-ranges therebetween.

Preferably, the cationic surfactants of the conditioner composition (B) are selected from, including its salts, of the general formula (I):

(I)

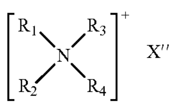

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and R4 denoting a radical comprising from 8 to 30 carbon atom; and X" is chosen from halides, phosphates, acetates, lactates, ($C_2$-$C_6$) alkyl sulfates, and alkyl- or alkylaryl-sulfonates.

In an embodiment, the at least two different cationic surfactants may be selected from cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, cetyltrimethylammonium chloride, cetyltrimethylammonium bromide, dipalmitoylethyl hydroxyethylmonium methosulfate, dicetyldimonium chloride (Varisoft 432 PPG), tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyl-dimethylamine, behenamidopropyldiethylamine, behenamidoethyldiethyl-amine, behenamidoethyldimethylamine, arachidamidopropyldimethylamine, arachidamidopropyidiethylamine, arachidamidoethyldiethylamine, arachidamidoethyldimethylamine, brassicamidopropyldimethylamine, or mixtures thereof.

In an embodiment, the at least two different cationic surfactants comprise cetrimonium chloride and behentrimonium chloride. Preferably, cetrimonium chloride ranges from about 0.1 to about 2 wt. % or about 0.2 to about 1.5 wt. % or about 0.5 to about 1 wt. %, based on the total weight of the composition, including ranges and sub-ranges therebetween, and the behentrimonium chloride ranges from about 0.5 to about 2 wt. % or about 1 to about 1.8 wt. % or about 1 to about 1.5 wt. %, based on the total weight of the composition, including ranges and sub-ranges therebetween. In a preferred embodiment, the weight ratio between the cetrimonium chloride to behentrimonium chloride of the conditioner composition (B) ranges from about 1:1 to about 1:4.

In a preferred embodiment, the fatty alcohol of the conditioner composition (B) is selected from, but not limited to, cetyl alcohol, stearyl alcohol, cetearyl alcohol, or a mixture thereof.

In a preferred embodiment, the first silicone of the conditioner composition (B) of the hair care system is present at a range from about 0.15 to about 0.6 wt. % or about 0.2 to about 0.4 wt. % or about 0.25 to about 0.35 wt. %, based on the total weight of the composition, including ranges and sub-ranges therebetween.

Preferably, but not limited to, the first silicone of the conditioner composition (B) is a polydialkylsiloxane, more preferably having a viscosity ranging from 5 cst to 1.000.000 cst. Even more preferably, the polydialkylsiloxane is selected from, but not limited to, dimethicones (also known as polydimethylsiloxanes).

In a preferred embodiment, the second silicone of the conditioner composition (B) of the hair care system is present at a range from about 0.6 to about 2.4 wt. % or about 0.7 to about 2.2 wt. % or about 0.8 to about 2.0 wt. %, based on the total weight of the composition, including ranges and sub-ranges therebetween.

Preferably, but not limited to, the second silicone of the conditioner composition (B) is an aminosilicone. More preferably, the aminosilicone is selected from, but not limited to, amodimethicones.

Particularly, when the first silicone is polydialkylsiloxane and the second silicone is aminosilicone, they are present, combined, at a range from about 0.7 to 3 wt. % or about 1 to about 2.5 wt. % or about 1.5 to about 2.0 wt. %, based on the total weight of the composition, including ranges and sub-ranges therebetween, and preferably, in a weight ratio of polydialkylsiloxane to aminosilicone ranging from about 5:1 to about 1:1 or about 4.5:1 to about 1.5:1 or about 4:1 to about 2:1 or about 4:1 to about 3:1, including ranges and sub-ranges therebetween. In various embodiments, the weight ratio of polydialkylsiloxane to aminosilicone is at about 5:1, 4.8:1, 4:5:1, 4.2; 1, 4:1, 3.8:1, 3.5:1, 3.2:1, 3:1, 2.8:1, 2.5:1, 2.2:1, 2:1, 1.8:1, 1.5:1, 1.4:1, 1.2:1, or 1:1.

Optionally, the conditioner composition (B) of the hair care system of the present invention may further comprise from 0.1 to 10 wt. % based on the total weight of the composition of additional ingredients, such as polyols, nonionic surfactants, plant oils, mineral oil, waxes, clays, preservatives, pH adjuster and fragrance.

Optionally, the hair care system of the present invention further comprises:

(C) a mask composition, comprising:

(a) from about 0.5 to about 2 wt. % of each of at least two different cationic surfactants, in a total amount of from about 1 to about 4 wt. % of cationic surfactant;

(b) from about 4 to about 8 wt. % or from about 4.5 to about 7 wt. % or from about 5 to about 6 wt. % of at least one fatty alcohol;

(c) from about 3.0 to about 6.0 wt. % of at least two silicones; and (d) water;

All weights being based on the total weight of the composition.

In a preferred embodiment, the weight ratio between the two cationic surfactants of the mask composition (C) ranges from about 1:1 to about 1:4. Preferably, the weight ratio between the at least two cationic surfactants can range from be about 1:1 or 1:1.5 or 1:2 or 1:2.5 or 1:3 or 1:3.5 or can range from about 1:1.5 to about 1:3.8 or about 1:2 to about 1:3.5 or about 1:2.2 to about 1:3.2 or about 1:2.5 to about 1:3 or about 1:2.5 to about 1:2.8, including ranges and sub-ranges therebetween.

The cationic surfactants of the mask composition (C) may be selected from, including its salts, of the general formula (I):

(I)

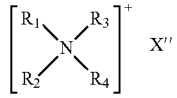

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and $R_4$ denoting a radical comprising from 8 to 30 carbon atom; and X" is chosen from halides, phosphates, acetates, lactates, ($C_2$-$C_6$) alkyl sulfates, and alkyl- or alkylaryl-sulfonates.

In an embodiment, the at least two different cationic surfactants comprise cetrimonium chloride and behentrimonium chloride. Preferably, cetrimonium chloride ranges from about 0.1 to about 2 wt. % or about 0.2 to about 1.5 wt. % or about 0.5 to about 1 wt. %, based on the total weight of the composition, including ranges and sub-ranges therebetween, and the behentrimonium chloride ranges from about 0.5 to about 2 wt. % or about 1 to about 1.8 wt. % or about 1.5 to about 1.8 wt. %, based on the total weight of the composition, including ranges and sub-ranges therebetween. In a preferred embodiment, the weight ratio between the cetrimonium chloride to behentrimonium chloride of the conditioner composition (B) ranges from about 1:1 to about 1:4.

In a preferred embodiment, the fatty alcohol of the mask composition (C) is selected from cetyl alcohol, stearyl alcohol, cetearyl alcohol, or a mixture thereof.

In a preferred embodiment, the first silicone of the mask composition (C) of the hair care system is present at a range from about 0.6 to about 1.2 wt. % or about 0.7 to about 1.0 wt. % or about 0.8 to about 0.9 wt. %, based on the total weight of the composition, including ranges and sub-ranges therebetween.

Preferably, but not limited to, the first silicone of the mask composition (C) is a polydialkylsiloxane. Preferably, the polydialkylsiloxane is selected from, but not limited to, dimethicones.

In a preferred embodiment, the second silicone of the mask composition (C) of the hair care system is present at a range from about 2.4 to about 4.8 wt. % or about 2.8 to about 4.4 wt. % or about 3.2 to about 4.0 wt. %, based on the total weight of the composition, including ranges and sub-ranges therebetween.

Preferably, but not limited to, the second silicone of the mask composition (C) is an aminosilicone. More preferably, the aminosilicone is selected from, but not limited to, amodimethicones.

Particularly, when the first silicone is polydialkylsiloxane and the second silicone is aminosilicone, they are present, combined, at a range from about 3.0 to about 6.0 wt. % based on the total weight of the composition, preferably, in a weight ratio of polydialkylsiloxane to aminosilicone ranging from about 1:1 to about 1:3, or about 1:1 to about 1:2.5 or about 1:1 to about 1:1.2 or about 1:1 to about 1:1.8 or about 1:1 to about 1:1.6 or about 1:1 to about 1:1.5 or about 1:1 to about 1:1.2, including ranges and sub-ranges therebetween.

Optionally, the mask composition of the hair care system of the present invention may further comprise from 0.1 to 10 wt. % based on the total weight of the composition of additional ingredients, such as polyols, nonionic surfactants, plant oils, mineral oil, waxes, clays, preservatives, pH adjuster and fragrance.

Ethoxylated Sulfate Anionic Surfactant

The at least one ethoxylated sulfate anionic surfactant having at least one degree of ethoxylation are selected from alkyl ether sulfates, their salts thereof, and mixtures thereof, including those having the formula:

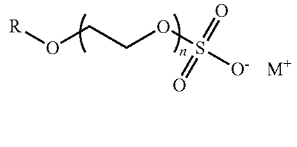

wherein:

R is an alkyl or alkenyl having from 6 to 24 (preferably, 8 to 18, more preferably, 12 to 18) carbon atoms;

n is a number having an average value of greater than at least 0.5, preferably between 1 and 4, such as from between 1 and 3 or such as from between 2 and 3 or such as from between 2 and 2.5; and M is a solubilizing cation such as alkali metal ions such as sodium or potassium, ammonium ions, substituted ammonium ions, or alkanolammonium ions such as monoethanolammonium or triethanolammonium ions.

Examples of useful alkyl ether sulfates, include, but are not limited to, sodium lauryl ether sulfate (SLES) or ammonium laureth sulfate.

In an embodiment, the alkyl ether sulfates of the present invention, include, but are not limited to, sodium lauryl ether sulfate (SLES) having n from between 2 and 3.

In a preferred embodiment, the amount of ethoxylated sulfate anionic surfactant of the shampoo composition (A) is at about 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, or 9 wt. %, based on the total weight of the composition.

The terms "comprising", "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "active material" as used herein with respect to the percent amount of an ingredient or raw material, refers to 100% activity of the ingredient or raw material.

"Cosmetically acceptable" means that the item in question is compatible with a keratinous substrate such as skin and hair. For example, a "cosmetically acceptable carrier" means a carrier that is compatible with a keratinous substrate such as skin and hair.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion.

This list of counter-ions, however, is non-limiting.

The expression "inclusive" for a range of concentrations means that the limits of the range are included in the defined interval.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Non-Ethoxylated Sulfate Anionic Surfactant

The at least one non-ethoxylated sulfate anionic surfactant are selected from alkyl sulfates including $C_6$-24 alkyl sulfates, $C_8$-18 alkyl sulfates, more preferably $C_{12}$-18 alkyl sulfates, their salts thereof, and mixtures thereof.

In some instances, useful alkyl sulfate salts include those having the formula:

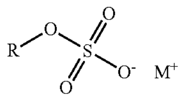

wherein:

R is an alkyl or alkenyl having from 6 to 24 (preferably, 8 to 18, more preferably, 12 to 18) carbon atoms; and M is a solubilizing cation such as alkali metal ions such as sodium or potassium, ammonium ions, substituted ammonium ions, or alkanolammonium ions such as monoethanolammonium or triethanolammonium ions.

Examples of useful alkyl sulfates include but are not limited to sodium lauryl sulfate (SLS), ammonium lauryl sulfate, and sodium dodecyl sulfate (SDS).

In a preferred embodiment, the amount of non-ethoxylated sulfate anionic surfactant of the shampoo composition (A) is at about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6 wt. %, based on the total weight of the composition.

Amphoteric Surfactants

In certain embodiments when the hair treatment composition of the present disclosure is a shampoo or a cleansing composition that contains at least one anionic surfactant, then the composition may further comprise at least one amphoteric surfactant. The amphoteric surfactants may, for example, be selected from betaines, alkyl sultaines, alkyl amphoacetates and alkyl amphodiacetates, alkyl amphoproprionates, salts thereof, or mixtures thereof.

In various embodiments, the betaines are selected from alkyl betaines, alkyl amidopropyl betaines, alkyl sulfobetaines (sultaines), or mixtures thereof.

In an embodiment, the amphoteric surfactants are selected from cocamidopropyl betaine, coco-betaine, or mixtures thereof.

The total amount of amphoteric surfactant(s) in the compositions may vary, but is typically from about 1.0 to about 5.0 wt %, based on the total weight of the composition. In some instance, the total amount of amphoteric surfactant(s) in the composition is from about 1.5 to about 4.0 wt %, from about 2.0 to about 3.5 wt %, from about 2.5 to about 3.1 wt %, based on the total weight of the composition, including ranges and sub-ranges therebetween.

Betaines

Exemplary useful betaines include, but are not limited to, those of the following formulae (XIIa-XIId):

(XIIa)

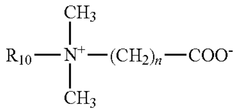

(XIIb)

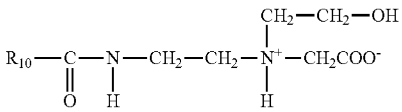

(XIIc)

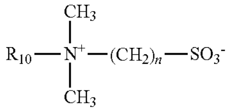

(XIId)

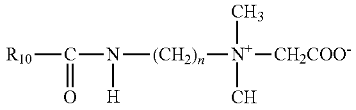

wherein:

$R_{10}$ is an alkyl group having from 8-18 carbon atoms; and n is an integer from 1 to 3.

Particularly useful betaines include, for example, cocobetaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or mixtures thereof. Particularly preferred betaines include coco-betaine and cocamidopropyl betaine.

Alkyl Sultaines

Non-limiting examples of alkyl sultaines include hydroxyl sultaines of formula (XIII):

(XIII)

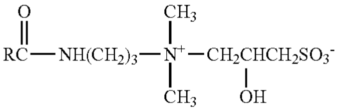

wherein R is an alkyl group having 8-18 carbon atoms.

More specific examples include, but are not limited to cocamidopropyl hydroxysultaine, lauryl hydroxysultaine, or mixtures thereof.

Alkyl Amphoacetates and Alkyl Amphodiacetates

Useful alkyl amphoacetates and alkyl amphodiacetates include those of formulae (XIV) and (XV):

(XIV)

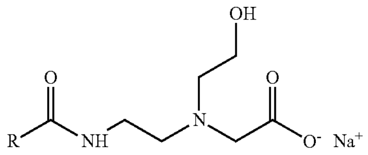

(XV)

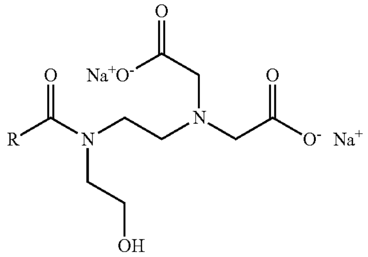

wherein R is an alkyl group having 8-18 carbon atoms. Although sodium is shown as the cation in the above formulae, the cation may be any alkali metal ion, such as sodium or potassium, ammonium ions, or alkanolammonium ions such as monoethanolammonium or triethanolammonium ions. A non-limiting example is sodium lauroamphoacetate.

Alkyl Amphopropionates

Exemplary and non-limiting examples of useful alkyl amphopropionates include cocoamphopropionate, caprylamphopropionate, cornamphopropionate, caproampho-propionate, oleoamphopropionate, isostearoamphopropionate, stearoamphopropionate, lauroamphopropionate, salts thereof, or mixtures thereof.

Water-Soluble Quaternary Ammonium Compound

The water-soluble quaternary ammonium compound derived from guar gum may include cationic guar gums described more particularly in U.S. Pat. Nos. 3,589,578 and 4,031,307, such as guar gums containing trialkylammonium cationic groups. Use is made, for example, of guar gums modified with a salt (e.g., chloride) of 2,3-epoxypropyltrimemylammonium. Mention may be made of guar hydroxypropyltrimonium chloride and hydroxypropyl guar hydroxypropyl trimonium chloride, such as those sold especially under the trade names Jaguar C13S, Jaguar C14S, Jaguar C17 and Jaguar C162 by the company Solvay.

Cationic Surfactants

The term "cationic surfactant" means a surfactant that may be positively charged when it is contained in the compositions according to the disclosure. This surfactant may bear one or more positive permanent charges or may contain one or more functional groups that are cationizable in the composition according to the disclosure.

The cationic surfactant(s) may also be chosen from optionally polyoxyalkylenated, primary, secondary or tertiary fatty amines, or salts thereof, and quaternary ammonium salts, and mixtures thereof. The fatty amines generally comprise at least one $C_8$-$C_{30}$ hydrocarbon-based chain.

In some cases, it is useful to use salts such as chloride salts of the quaternary ammonium compounds.

A. Examples of quaternary ammonium salts that may especially be mentioned include: those corresponding to the general formula (I) below:

(I)

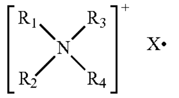

wherein $R_1$ and $R_4$, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R_1$, $R_2$, $R_3$ and $R_4$ denoting a radical comprising from 8 to 30 carbon atom and preferably from 12 to 24 carbon atoms; and X"" is chosen from halides, phosphates, acetates, lactates, ($C_2$-$C_6$) alkyl sulfates, and alkyl- or alkylaryl-sulfonates. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; X is an anion chosen from the group of halides, phosphates, acetates, lactates, ($C_1$-$C_4$)alkyl sulfates, and ($C_1$-$C_4$)alkyl- or ($C_1$-$C_4$) alkylarylsulfonates.

The halides may be chosen from chlorides and bromides.

Among the quaternary ammonium salts of formula (I), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium (behentrimonium), distearyldimethylammonium, cetyltrimethylammonium (cetrimonium) or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

B. a quaternary ammonium salt of imidazoline, such as, for example, those of formula (II) below:

(II)

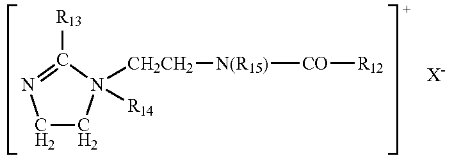

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat W 75 by the company Rewo;

C. a quaternary diammonium or triammonium salt, in particular of formula (III):

(III)

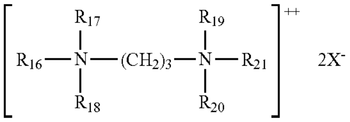

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$)($R_{17a}$)($R_{18a}$)N—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), D. Cationic/cationizable surfactants, for example of the general structure

R4-A-R5-B wherein R4 is a saturated or unsaturated, straight or branched alkyl chain with 8 to 24 C atoms, R5 is a straight or branched alkyl chain with 1 to 4 C atoms, A is selected from,

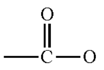

and

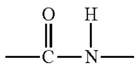

and B is selected from

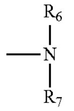

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms,

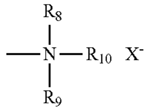

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms and X is an anion such as chloride, bromide, and methosulfate.

In some instances, $R_4$ is saturated or unsaturated, straight or branched alkyl chain with 10 to 24 C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants or amphiphilic surfactants may be chosen from fatty alkylamines, preferably, fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

In some cases, the compositions of the instant disclosure include at least one cationic surfactant selected from stearamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, benzoic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and mixtures thereof. In particular, lactic acid or tartaric acid or mixtures thereof are useful, especially in combination with fatty dimethylamines such as, for example, stearamidopropyl dimethylamine.

In various embodiments, the at least two different cationic surfactants may be selected from cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, cetyltrimethylammonium chloride, cetyltrimethylammonium bromide, dipalmitoylethyl hydroxyethylmonium methosulfate, dicetyldimonium chloride (Varisoft 432 PPG), tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyl-dimethylamine, behenamidopropyldiethylamine, behenamidoethyldiethyl-amine, behenamidoethyldimethylamine, arachidamidopropyldimethylamine, arachidamido-propyidiethylamine, arachidamidoethyldiethylamine, arachidamidoethyldimethylamine, brassicamidopropyldimethylamine, or mixtures thereof.

In an embodiment, the at least two different cationic surfactants comprise cetrimonium chloride and behentrimonium chloride.

Fatty Alcohols

The fatty alcohols that may be used in the composition of the disclosure include, but are not limited to, non-alkoxylated, saturated or unsaturated, linear or branched, and have from 6 to 60 carbon atoms, such as from 8 to 30 carbon atoms.

The fatty alcohols of the present disclosure are chosen from solid and liquid fatty alcohols.

The saturated liquid fatty alcohols can be branched. They can optionally comprise, in their structure, at least one aromatic or non-aromatic ring. They can be acyclic.

The unsaturated liquid fatty alcohols exhibit, in their structure, at least one double or triple bond, and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

Liquid fatty alcohols may be selected, for example, from octyldodecanol, 2-butyloctanol, 2-hexyldecanol, 2-undecylpentadecanol, oleyl alcohol or linoleyl alcohol, isostearyl alcohol, or mixtures thereof.

Solid fatty alcohols may be crystalline, amorphous, or pasty. The solid fatty alcohols of the present invention are solid at room temperature (25° C.) and at atmospheric pressure (1 atm), and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene, or liquid petroleum jelly) to at least 1% by weight.

In one embodiment, the solid fatty alcohols preferably have a melting point of greater than or equal to 28° C. and have a viscosity, at a temperature of 40° C. and at a shear rate of 1 s−1, of greater than or equal to 1 Pa·s.

In an embodiment, the melting point of the fatty alcohols ranges from 30° C. to 250° C., such as from 32° C. to 150° C., or from 35° C. to 150° C.

The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 6 to 60 carbon atoms, such as from 10 to 50 carbon atoms, or from 12 to 24 carbon atoms.

The solid fatty alcohols preferably have the structure of the following formula:

R—OH in which R especially denotes a $C_6$-$C_{60}$, for example, $C_8$-$C_{60}$, preferably $C_{10}$-$C_{50}$ or even $C_{12}$-$C_{30}$ alkyl group, R possibly being substituted with one or more hydroxyl groups, R possibly being branched. The solid fatty alcohols of the invention may be non-oxyalkylenated and/or non-glycerolated. These fatty alcohols may be constituents of animal or plant waxes.

The solid fatty alcohol may represent a mixture of fatty alcohols, which means that several species of fatty alcohol may coexist, in the form of a mixture, in a commercial product. One example of such a commercial product is cetearyl alcohol, a mixture of cetyl alcohol and stearyl alcohol, commercially available under the trade name of LANETTE O OR from the company BASF. Cetyl alcohol may also be commercially available under the tradename of LANETTE 16 from the company BASF.

In an embodiment, the solid fatty alcohols of the present invention may be chosen from myristyl alcohol, cetyl alcohol, stearyl alcohol, cetearyl alcohol, or mixtures thereof, octyldodecanol, 2-butyloctanol, 2-hexyldecanol, 2-undecylpentadecanol, oleic alcohol, linoleic alcohol, behenyl alcohol, or mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol, and 2-hexadecyl-1-eicosanol, or mixtures thereof.

In an embodiment of the present invention, the fatty alcohol is chosen from non-alkoxylated, saturated or unsaturated, linear or branched fatty alcohol having from 6 to 60 carbon atoms is chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, behenyl alcohol, 2-dodecylhexadecanol, 2-tetradecyl-1-octadecanol, 2-tetradecyl-1-eicosanol, 2-hexadecyl-1-octadecanol and 2-hexadecyl-1-eicosanol, octyldodecanol, 2-butyloctanol, 2-hexyldecanol, 2-undecylpentadecanol, oleyl alcohol or linoleyl alcohol, isostearyl alcohol, or mixtures thereof In an embodiment, the at least one nonionic surfactant is selected from alkyl polyglucosides, fatty alcohols, alkoxylated fatty alcohols, sorbitan derivatives, glyceryl esters, or mixtures thereof.

In an embodiment, when the composition of the present disclosure is a conditioner or rinse-off or leave-in mask composition, the composition comprises at least one nonionic surfactant selected from fatty alcohols.

In an embodiment of the present invention, the fatty alcohol is chosen from cetyl alcohol.

In an embodiment of the present invention, the fatty alcohol is chosen from cetearyl alcohol.

In an embodiment of the present invention, the fatty alcohol comprises cetyl alcohol and cetearyl alcohol.

In an embodiment of the present invention, the fatty alcohol comprises cetyl alcohol and stearyl alcohol.

In an embodiment of the present invention, the fatty alcohol is chosen from cetyl alcohol, stearyl alcohol, cetearyl alcohol, or mixtures thereof.

In an embodiment, the fatty alcohols of the present invention are chosen from liquid fatty alcohol, solid fatty alcohols, or mixtures thereof.

Silicone Emulsions

The shampoo composition (A) of the hair care system of the present invention also comprises an oil-in-water emulsion having a particle size D50 of less than 350 nm, and comprising:

- a silicone mixture comprising (i) a polydialkylsiloxane comprising trialkylsilyl end groups, having a viscosity at 25° C. ranging from 40,000 to 100,000 mPa·s and (ii) an aminosilicone having a viscosity at 25° C. ranging from 1,000 to 15,000 mPa·s and an amine number ranging from 2 to 10 mg of KOH per gram of aminosilicone;
- a surfactant mixture comprising one or more non-ionic surfactants, said mixture having an HLB ranging from 10 to 16, and
- water.

In the oil-in-water, or silicone-in-water, emulsion, according to the invention, a liquid phase (the dispersed phase) is advantageously dispersed in another liquid phase (the continuous phase); in the present invention, the mixture of silicones, or silicone phase, is dispersed in the aqueous continuous phase.

The mixture of silicones (or silicone mixture) comprises one or more polydialkylsiloxanes comprising trialkylsilyl end groups, preferably of formula (I):

R'3SiO(R'2SiO)*p*SiR'3 in which:

- R', which may be identical or different, is a monovalent hydrocarbon-based radical having from 1 to 18 carbon atoms, preferably from 1 to 6 carbon atoms, better still from 1 to 3 carbon atoms, even better still a methyl radical, and
- p is an integer ranging from 500 to 2,000, better still from 1,000 to 2,000.

The polydialkylsiloxanes comprising trialkylsilyl end groups according to the invention have a viscosity ranging from 40,000 to 100,000 mPa·s (preferably 100,000 excluded) at 25° C., preferably ranging from 40,000 to 70,000 mPa·s at 25° C., better still from 51,000 to 70,000 mPa·s at 25° C.

The polydialkylsiloxanes comprising trialkylsilyl end groups according to the invention are preferably linear, but they may comprise, in addition to the R'2SiO2/2 units (D-units), additional RSiO3/2 units (T-units) and/or SiO4/2 units (Q-units), in which R', which may be identical or different, is a $C_1$-$C_{18}$ monovalent hydrocarbon-based radical.

In formula (I), R', which may be identical or different, is preferably:

- an alkyl, preferably $C_1$-$C_{28}$ alkyl, radical, such as the radicals methyl, ethyl, n-propyl, isopropyl, 1-n-butyl, 2-n-butyl, isobutyl, tert-butyl, n-pentyl, isopentyl, neopentyl, tert-pentyl, hexyl and in particular n-hexyl, heptyl and in particular n-heptyl, octyl and in particular n-octyl, isooctyl, 2,2,4-trimethylpentyl; nonyl and in particular n-nonyl; decyl and in particular n-decyl; dodecyl and in particular n-dodecyl; octadecyl and in particular n-octadecyl;
- an alkenyl radical such as vinyl and allyl;
- a cycloalkyl radical such as cyclopentyl, cyclohexyl, cycloheptyl and methylcyclohexyl;
- an aryl radical such as phenyl, naphthyl, anthryl and phenanthryl;
- an alkaryl radical such as the radicals o-, m- and p-tolyl; xylyl, ethylphenyl;
- an aralkyl radical such as benzyl and phenylethyl.

Preferentially, R' is a methyl radical.

Preferably, the polydialkylsiloxanes comprising trialkylsilyl end groups are polydimethylsiloxanes (PDMSs) comprising trialkylsilyl end groups.

The silicone mixture also comprises one or more aminosilicones, preferably of formula (II): XR2Si(OSiAR)n (OSiR2)mOSiR2X in which:

- R, which may be identical or different, is a monovalent hydrocarbon-based radical having from 1 to 18 carbon atoms, preferably from 1 to 6 carbon atoms, better still from 1 to 3 carbon atoms, even better still a methyl radical,
- X, which may be identical or different, represents R or a hydroxyl (OH) or a C1-C6 alkoxy group; preferably X is R, that is to say a monovalent hydrocarbon-based radical having from 1 to 18 carbon atoms, preferably from 1 to 6 carbon atoms, better still from 1 to 3 carbon atoms, even better still a methyl radical,
- A is an amino radical of formula —R1-[NR2-R3-]XNR22, or the protonated form of this amino radical, with
- R1 representing a $C_1$-$C_6$ alkylene radical, preferably a $—CH_2CH_2CH_2—$ or $—CH_2CH(CH_3)CH_2—$ radical,
- $R_2$, which may be identical or different, being a hydrogen atom or a $C_1$-$C_4$ alkyl radical, preferably a hydrogen atom, $R_3$ being a $C_1$-$C_6$ alkylene radical, preferably a —$CH_2CH_2$— radical, x being 0 or 1;

m and n are integers such that m+n ranges from 50 to 1000, better still from 50 to 600.

Preferably, A is an amino radical of formula —R1-[NR2-R3-]XNR22, or the protonated form of this amino radical, with R1 being —$CH_2CH_2CH_2$— or —$CH_2CH(CH_3)CH_2$—, R2 being hydrogen atoms, R3 being —$CH_2CH_2$— and x being equal to 1.

Preferably, R, which may be identical or different, is:

an alkyl, preferably $C_1$-$C_{28}$ alkyl, radical, such as the radicals methyl, ethyl, n-propyl, isopropyl, 1-n-butyl, 2-n-butyl, isobutyl, tert-butyl, n-pentyl, isopentyl, neopentyl, tert-pentyl, hexyl and in particular n-hexyl, heptyl and in particular n-heptyl, octyl and in particular n-octyl, isooctyl, 2,2,4-trimethylpentyl; nonyl and in particular n-nonyl; decyl and in particular n-decyl; dodecyl and in particular n-dodecyl; octadecyl and in particular n-octadecyl;

an alkenyl radical such as vinyl and allyl;

a cycloalkyl radical such as cyclopentyl, cyclohexyl, cycloheptyl and methylcyclohexyl;

an aryl radical such as phenyl, naphthyl, anthryl and phenanthryl;

an alkaryl radical such as the radicals o-, m- and p-tolyl; xylyl, ethylphenyl;

an aralkyl radical such as benzyl and phenylethyl.

Preferentially, R is a methyl radical.

The aminosilicones according to the invention have a viscosity, measured at 25° C., ranging from 1,000 to 15,000 mPa·s, preferably ranging from 1,500 to 15,000 mPa·s.

The aminosilicones according to the invention have an amine number ranging from 2 to 10 mg of KOH per gram of aminosilicone; preferably from 3.5 to 8 mg.

The molar percentage of amine function is preferably between 0.3 and 8 mol %.

As examples of aminosilicones, mention may be made of aminosilicones comprising trialkylsilyl end groups; preferably aminoethylaminopropylmethylsiloxanes comprising trialkylsilyl end groups, even better still copolymers of aminoethylaminopropylmethylsiloxane comprising trialkylsilyl end groups/dimethylsiloxane.

The amino radical A may be partially or totally protonated, for example by addition of acids to the aminosilicone, so as to obtain the salified form of said amino radical.

As acids that may be used, mention may be made of linear or branched carboxylic acids having from 3 to 18 carbon atoms, such as formic acid, acetic acid, propionic acid, butyric acid, pivalic acid, sorbic acid, benzoic acid or salicylic acid. Preferably, the acids may be used in a proportion of from 0.1 to 2.0 mol per mole of amino radical A in the aminosilicone of formula (II).

The silicone mixture preferably comprises (i) one or more polydialkylsiloxanes comprising trialkylsilyl end groups, having a viscosity, at 25° C., ranging from 40,000 to 100,000 mPa·s, in an amount of from 70% to 90% by weight, preferably from 75% to 85% by weight, and (ii) one or more aminosilicones having a viscosity, at 25° C., ranging from 1,000 to 15,000 mPa·s and an amine number ranging from 2 to 10 mg of KOH per gram of aminosilicone, in an amount of from 10% to 30% by weight, in particular from 15% to 25% by weight, relative to the total weight of the silicone mixture.

The oil-in-water emulsion also comprises a surfactant mixture which comprises one or more non-ionic surfactants; said surfactant mixture may optionally comprise one or more cationic surfactants.

Said surfactant mixture has an HLB ranging from 10 to 16.

The non-ionic surfactants that may be used may be chosen from alcohols, α-diols and (C1-20)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or else these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

Mention may also be made of non-ionic surfactants of alkyl(poly)glycoside type, represented especially by the following general formula:

$$R1O—(R2O)_t-(G)_v$$

in which:

$R_1$ represents a linear or branched alkyl or alkenyl radical comprising 6 to 24 carbon atoms and especially 8 to 18 carbon atoms, or an alkylphenyl radical of which the linear or branched alkyl radical comprises 6 to 24 carbon atoms and especially 8 to 18 carbon atoms;

$R_2$ represents an alkylene radical comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkyl(poly)glycoside surfactants are compounds of the formula described above in which:

R1 denotes a linear or branched, saturated or unsaturated alkyl radical comprising from 8 to 18 carbon atoms, R2 represents an alkylene radical comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. $C_8/C_{16}$ alkyl(poly)glucosides 1,4, and in particular decyl glucosides and caprylyl/capryl glucosides, are most particularly preferred.

Among commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or else the products sold by the company Chem Y under the name AG10 LK.

Preferably, use is made of $C_8$/Cm-alkyl (poly)glycosides 1,4, in particular as an aqueous 53% solution, such as those sold by Cognis under the reference Plantacare® 818 UP.

The mono- or polyglycerolated surfactants preferably comprise an average number of glycerol groups ranging from 1 to 30, in particular from 1 to 10, better still from 1.5 to 5. They preferably correspond to one of the following formulae:

$RO[CH_2CH(CH_2OH)O]mH,$ $RO[CH_2CH(OH)CH_2O]mH$ or $RO[CH(CH_2OH)CH_2O]mH;$ in which:

R represents a saturated or unsaturated, linear or branched hydrocarbon-based (in particular alkyl or alkenyl) radical comprising 8 to 40 carbon atoms, in particular 10 to 30 carbon atoms, optionally comprising one or more heteroatoms such as O and N; and m is an integer ranging from 1 to 30, preferably from 1 to 10, better still from 1.5 to 6.

In particular, R may comprise one or more hydroxyl and/or ether and/or amide groups. Preferably, R is a mono- or polyhydroxylated $C_{10}$-$C_{20}$ alkyl or alkenyl radical.

Mention may be made of polyglycerolated (3.5 mol) hydroxylauryl ether, such as the product Chimexane® NF from Chimex.

Mention may also be made of (poly)ethoxylated fatty alcohols preferably comprising one or more saturated or unsaturated, linear or branched hydrocarbon-based chains comprising 8 to 30 carbon atoms, preferably from 12 to 22 carbon atoms, optionally substituted with one or more hydroxyl (OH) groups, in particular 1 to 4 hydroxyl groups.

When the chain is unsaturated, it may comprise one to three conjugated or non-conjugated carbon-carbon double bonds.

The (poly)ethoxylated fatty alcohols preferably correspond to formula (II):

$R3\text{-}(OCH_2CH_2)cOH$ in which:

R3 represents a linear or branched alkyl or alkenyl radical comprising 8 to 40 carbon atoms and in particular 8 to 30 carbon atoms, optionally substituted with one or more, in particular 1 to 4, hydroxyl groups; and c is an integer ranging from 1 to 200, preferably from 2 to 150, or even from 4 to 50 and even better still from 8 to 30.

The (poly)ethoxylated fatty alcohols are more particularly fatty alcohols comprising 8 to 22 carbon atoms, oxyethylenated with 1 to 30 mol of ethylene oxide (1 to 30 EO); mention may in particular be made of lauryl alcohol 2 EO; lauryl alcohol 3 EO; decyl alcohol 3 EO; decyl alcohol 5 EO and oleyl alcohol 20 EO.

The non-ionic surfactants may advantageously be chosen from:

(i) (poly)oxyalkylenated, in particular (poly)ethoxylated, fatty alcohols, and in particular those of formula: $R3\text{-}(OCH_2CH_2)_cOH$ in which:

$R_3$ represents a linear or branched alkyl or alkenyl radical comprising 8 to 40 carbon atoms and in particular 8 to 30 carbon atoms, optionally substituted with one or more, in particular 1 to 4, hydroxyl groups; and c is an integer ranging from 1 to 200, in particular from 2 to 150, or even from 4 to 50 and even better still from 8 to 20;

(ii) (poly)oxyalkylenated ($C_8$-$C_{32}$)alkyl phenyl ethers, in particular comprising from 1 to 200, better still from 1 to 30 mol of ethylene oxide;

(iii) polyoxyalkylenated esters of $C_8$-$C_{32}$ fatty acids and of sorbitan, in particular polyoxyethylenated esters of $C_8$-$C_{32}$ fatty acids and of sorbitan, preferably having from 2 to 40 ethylene oxide units, better still from 2 to 20 ethylene oxide (EO) units; in particular polyoxyethylenated esters of $C_{10}$-$C_{24}$ fatty acids and of sorbitan, preferably having from 2 to 40 ethylene oxide units, better still from 2 to 20 ethylene oxide (EO) units; and (iv) polyoxyethylenated esters of $C_8$-$C_{32}$ fatty acids, preferably having from 2 to 150 ethylene oxide units; in particular polyoxyethylenated esters of $C_{10}$-$C_{24}$ fatty acids, comprising in particular 2 to 150 ethylene oxide (EO) units.

The non-ionic surfactants may advantageously be chosen from alkyl ethers and alkyl esters of polyalkylene glycol, in particular of polyethylene glycol.

Mention may in particular be made of:

polyethylene glycol octyl ether; polyethylene glycol lauryl ether; polyethylene glycol tridecyl ether; polyethylene glycol cetyl ether; polyethylene glycol stearyl ether; and most particularly trideceth-3, trideceth-10 and steareth-6;

polyethylene glycol nonylphenyl ether; polyethylene glycol dodecylphenyl ether; polyethylene glycol cetylphenyl ether; polyethylene glycol stearylphenyl ether;

polyethylene glycol sorbitan monostearate, polyethylene glycol sorbitan monooleate;

polyethylene glycol stearate, and in particular PEG100 stearate.

Even better still, the non-ionic surfactants may be chosen from Steareth-6, PEG100 stearate, trideceth-3 and trideceth-10, and mixtures thereof; most particularly, a mixture comprising these four non-ionic surfactants.

The surfactant mixture may optionally comprise one or more cationic surfactants, which may be chosen from tetraalkylammonium, tetraarylammonium and tetraalkylarylammonium salts, in particular halides, and most particularly from cetrimonium or behentrimonium salts, in particular halides, better still chlorides.

The oil-in-water emulsion preferably comprises the surfactant mixture in a total amount ranging from 5% to 15% by weight, in particular from 8% to 15% by weight, even better still from 10% to 12% by weight, relative to the total weight of the emulsion.

The oil-in-water emulsion preferably comprises the non-ionic surfactant(s) in a total amount ranging from 5% to 15% by weight, in particular from 8% to 15% by weight, even better still from 10% to 12% by weight, relative to the total weight of the emulsion.

The oil-in-water emulsion preferably comprises the cationic surfactant(s), when they are present, in a total amount ranging from 0.5% to 1.5% by weight relative to the total weight of the emulsion.

The oil-in-water emulsion preferably comprises the silicone mixture in a total amount ranging from 40% to 60% by weight, in particular from 45% to 55% by weight, relative to the total weight of the emulsion.

The oil-in-water emulsion preferably comprises the polydialkylsiloxane(s) comprising trialkylsilyl end groups in a total amount ranging from 35% to 45% by weight, in particular from 38% to 42% by weight, relative to the total weight of the emulsion. The oil-in-water emulsion preferably comprises the aminosilicone(s) in a total amount ranging from 5% to 15% by weight, in particular from 8% to 12% by weight, relative to the total weight of the emulsion.

The oil-in-water emulsion preferably comprises water in a total amount ranging from 25% to 50% by weight, in particular from 30% to 45% by weight, even better still from 35% to 42% by weight, relative to the total weight of the emulsion.

The oil-in-water emulsion may also comprise a preservative, such as phenoxyethanol, in an amount ranging from 0.5% to 1% by weight relative to the total weight of the emulsion.

A process for preparing the oil-in-water emulsion preferably comprises:

- a step of mixing one or more polydialkylsiloxanes comprising trialkylsilyl end groups, having a viscosity, at 25° C., ranging from 40 000 to 100 000 mPa·s, and one or more aminosilicones having a viscosity, at 25° C., ranging from 1000 to 15 000 mPa·s and an amine number ranging from 2 to 10 mg of KOH per gram of aminosilicone; at a temperature of from 15° C. to 40° C., in particular at 25° C., in order to obtain a fluid mixture of silicones; then
- a step of adding a surfactant mixture comprising one or more non-ionic surfactants, said mixture having an HLB ranging from 10 to 16, to said fluid mixture of silicones, in order to obtain an emulsified silicone mixture; then
- a step of homogenizing said emulsified silicone mixture, followed by
- a step of adding water, in particular demineralized water, preferentially in steps, in order to obtain an oil-in-water emulsion having a particle size D50 of less than 350 nm.

The preparation process may also comprise an additional step of adding one or more preservatives.

The pH of the oil-in-water emulsion is generally between 4 and 6.

The oil-in-water emulsion has a particle size D50 of less than 350 nm, in particular of between 100 and 300 nm, better still between 150 and 250 nm, or even between 160 and 200 nm.

This size corresponds to the average hydrodynamic particle diameter.

The particle size D50 is expressed by volume. It can be measured using a ZetaSizer device from Malvern, UK, model Nano-ZS, based on the "Photon Correlation Spectroscopy (PCS)" method.

Method for Measuring the Particle Size

The particle size of the emulsion is measured using a ZetaSizer device from Malvern, UK, model Nano-ZS, based on the "Photon Correlation Spectroscopy (PCS)" method.

The particle size D50 is measured when the evaluation algorithm is "cumulant analysis".

0.5 g of the emulsion is placed in a 250 ml beaker, 100 ml of demineralized water are added and mixing is carried out in order to obtain the solution to be tested. The solution to be tested is placed in the measuring vessel (or cell) and introduced into the measuring device.

The size D50 corresponds to the particle diameter value at 50% in cumulative distribution.

For example, if D50=170 nm, this means that 50% of the particles have a size of greater than 170 nm, and that 50% of the particles have a size of less than 170 nm.

It should be recalled that this distribution is by volume.

Method for Measuring the Viscosity

The viscosities, in particular of the silicone compounds, are measured at 25° C., 1 atm.

To measure viscosities of between 1,000 and 40,000 mPa·s at 25° C., use may be made of an Anton Paar rheometer, model MCR101, cylinder geometry, single gap: CC27 spindle, shear ratel s−1 for 2 minutes, at 25° C.

To measure viscosities of between 40,000 and 100,000 mPa·s at 25° C., use may be made of an Anton Paar rheometer, model MCR101, 25-6 cone (cone-plate geometry, 25 mm in diameter/6° cone); Zero gap, shear rate 1 s−1 for 2 minutes, at 25° C.

Three measurements are carried out for each sample, and the viscosity value is taken at 60 seconds. The MCR Rheometer Series products operate according to the USP convention (US Pharmacopeia Convention, 912—Rotational Rheometer methods).

Method for Measuring the Amine Number

The amine number can be measured by acid-based titration, using a potentiometer [Make: Veego; model VPT-MG].

0.6 g of sample is placed in a 500 ml beaker and a 1:1 toluene-butanol mixture is added, then mixing is carried out.

The solution is titrated with a 0.1 N HCl solution. A determination of the zero value (Vblank) is also carried out with the 1:1 toluene-butanol mixture alone.

The amine number is calculated by means of the formula:

$$56.11\times(V-V\text{Blank})\times N/W \text{ mg KOH/g of sample}$$

With V=volume of HCl required (in ml), VBlank=volume of HCl required for the zero value (in ml); N=normality of HCl, i.e. 0.1, and W=weight of the sample (in g).

HLB Values

The term HLB relates to the hydrophobicity-lipophilicity balance of a surfactant. It can be measured experimentally or calculated.

In the present application, the HLB values are the values at 25° C.

The HLB values can be calculated by means of the following equation: HLB=(E+P)/5, in which E is the % by weight of oxyethylene and P is the % by weight of polyol, as is described in the publication Griffin, J. Soc. Cosm. Chem. 1954 (vol. 5, n° 4), pages 249-256.

The HLB values can also be determined experimentally according to the book by Puisieux and Seiller, entitled "Galenica 5: Les systemes disperses [Galenics 5: Dispersed systems]—Volume I—Agents de surface et emulsions [Surface agents and emulsions]—Chapter IV—Notions de HLB et de HLB critique [Notions of HLB and of critical HLB], pages 153-194—paragraph 1.1.2. Determination de HLB par voie experimentale [Experimental determination of HLB], pages 164-180".

Preferably, the HLB values that will be taken into account are those obtained by calculation, in particular in the following way: "calculated HLB"=20×(molar mass of the hydrophilic part/total molar mass).

Thus, for an oxyethylenated fatty alcohol, the hydrophilic part corresponds to the oxyethylene units fused to the fatty alcohol and the "calculated HLB" then corresponds to the "HLB according to Griffin".

For an ester or an amide, the hydrophilic part is generally defined as being beyond the carbonyl group, starting from the fatty chain(s).

The HLB values of non-ionic surfactants can also be calculated by means of the Davies formula, as described in Davies JT (1957), "A quantitative kinetic theory of emulsion type, I. Physical chemistry of the emulsifying agent", Gas/Liquid and Liquid/Liquid Interface (Proceedings of the International Congress of Surface Activity): 426-438.

According to this formula, the HLB value is obtained by adding the hydrophilic/hydrophobic contribution the to the constituent groups in the surfactant:

$$HLB=(\text{number of hydrophilic groups})-n(\text{number of groups per CH2 group})+7.$$

The HLB values of some cationic surfactants are given in Table IV, in "Cationic emulsifiers in cosmetics", GODFREY, J. Soc. Cosmetic Chemists (1966) 17, pages 17-27.

When two surfactants A and B, of known HLB values, are mixed, the HLBMix corresponds to the HLB of the mixture and can be expressed by the following equation:

$$HLB\text{Mix}=(WAHLBA+WBHLBB)/(WA+WB)$$

in which WA is the amount (weight) of the 1st surfactant A and WB the amount of the 2nd surfactant B, and HLBA and HLBB are the HLB values of the surfactant A and of the surfactant B.

Preferably, the composition according to the invention comprises the oil-in-water emulsion in a total amount ranging from 0.1% to 10% by weight, better still from 0.2% to 8% by weight, preferentially from 0.5% to 6% by weight, relative to the total weight of the composition.

Preferably, the composition according to the invention comprises the oil-in-water emulsion in a total amount ranging from 0.1% to 10% by weight, better still from 0.2% to 8% by weight, preferentially from 0.5% to 6% by weight, relative to the total weight of the composition, and the emulsion has a solids (or active material) content of between 40% and 60% by weight, in particular 45% to 55% by weight, relative to the total weight of the emulsion.

Silicones

Silicones include, but are not limited to, polyorganosiloxanes, polyalkylsiloxanes, polyarylsiloxanes, polyalkarylsiloxanes, polyestersiloxanes, or mixtures thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane or mixtures thereof.

In some instances, the compositions include (or exclude) one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, or mixtures thereof.

The hair treatment compositions may include (or exclude) one or more silicone oils, for example one or more non-phenyl silicone oils and/or one or more phenyl silicone oils. The silicone oil is preferably apolar. An "apolar silicone oil" is intended to denote a silicon oil that does not comprise any ionic or ionisable group(s), and preferably does not comprise any oxyalkylenated($C_2$-$C_4$) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

- polydimethylsiloxanes (PDMSs);
- PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference Abil Wax 9801 from Evonik Goldschmidt;
- PDMSs comprising aliphatic groups, or functional groups such as hydroxyl, thiol and/or amine groups;
- polyalkylmethylsiloxanes substituted with functional groups such as hydroxyl, thiol and/or amine groups; and
- polysiloxanes modified with fatty acids, fatty alcohols or polyoxyalkylenes, or mixtures thereof.

Preferably, non-volatile, non-phenyl silicone oils are chosen from polydimethylsiloxanes, alkyl dimethicones, and also PDMSs comprising aliphatic groups, in particular $C_2$-$C_{24}$ alkyl groups, and/or functional groups such as hydroxyl, thiol, and/or amine groups.

The non-phenyl silicone oil may be chosen in particular from silicones of the following formula:

(XVIII)

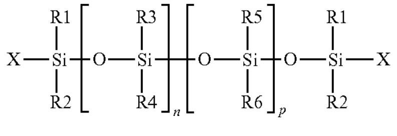

wherein:

- $R_1$, $R_2$, $R_5$, and $R_6$, which may be identical or different, are independently chosen from alkyl radicals containing 1 to 6 carbon atoms,
- $R_3$ and $R_4$, which may be identical or different, are independently chosen from alkyl radicals containing from 1 to 6 carbon atoms, a vinyl radical, an amine radical, or a hydroxyl radical,
- X is an alkyl radical containing from 1 to 6 carbon atoms, a hydroxyl radical, or an amine radical, and n and p are integers chosen so as to have a fluid compound, in particular of which the viscosity at 25° C. is between 9 centistokes (cSt) and 800 000 (cSt).

As non-volatile, non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500,000 by the company Bluestar, and the product sold under the name Dow Corning 200 Fluid 500,000 cSt by the company Dow Corning, the substituents $R_1$ to $R_6$ and X represent a methyl group, and p and n are such that the viscosity is 60,000 cSt, for example the product sold under the name Dow Corning 200 Fluid 60,000 CS by the company Dow Corning, and the product sold under the name Wacker Belsil DM 60,000 by the company Wacker, the substituents R1 to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Hair Care Method

In an embodiment, the present invention relates to a hair care method comprising the steps of:

(1) Applying the shampoo composition (A) of the hair care system on wet hair and washing the hair, the shampoo composition (A) comprising:

(a) from about 5 to about 15 wt. % of at least one ethoxylated sulfate anionic surfactant having at least one degree of ethoxylation and/or its salt thereof;

(b) from about 1 to about 10 wt. % of at least one non-ethoxylated sulfate anionic surfactant and/or its salt thereof;

(c) from about 1 to about 5 wt. % of at least one amphoteric surfactant;

(d) from about 0.1 to 3 wt. % of at least one water-soluble quaternary ammonium compound;

(e) an oil-in-water emulsion having a particle size D50 of less than 350 nm, and comprising:

a silicone mixture comprising:

(i) a polydialkylsiloxane comprising trialkylsilyl end groups, having a viscosity at 25° C. ranging from 40,000 to 100,000 mPa·s; and (ii) an aminosilicone having a viscosity at 25° C. ranging from 1,000 to 15,000 mPa·s and an amine number ranging from 2 to 10 mg of KOH per gram of aminosilicone;

a surfactant mixture comprising one or more non-ionic surfactants, said mixture having an HLB ranging from 10 to 16;

water.

All weights being based on the total weight of the shampoo composition (A);

(2) Rinsing the hair with water;

(3) Applying, on wet hair, the conditioner composition (B) of the hair care system, which comprises:

(a) from about 0.5 to about 2 wt. % of each of at least two different cationic surfactants, in a total amount of from about 1 to about 4 wt. % of cationic surfactant;

(b) from about 3.0 to about 5.0 wt. % of at least one fatty alcohol;

(c) from about 0.7 to about 3.0 wt. % of at least two silicones;

(d) water;

All weights being based on the total weight of the conditioner composition (B);

(4) Rinsing the hair with water;

(5) Optionally applying, on wet hair, the mask composition (C) of the hair care system, which comprises:

(a) from about 0.5 to about 2.0 wt. % of each of at least two different cationic surfactants derived from quaternary ammonium salts with a $C_{12}$-$C_{22}$ chain length, in a total amount of from about 1.0 to about 4.0 wt. % of cationic surfactant;

(b) from about 4 to about 8 wt. % of at least one fatty alcohol;

(c) from about 3.0 to about 6.0 wt. % of at least two silicones; and (d) water;

All weights being based on the total weight of the mask composition (C).

Method for Manufacturing a Shampoo Composition

The shampoo composition of the present invention is achieved by combining from about 5 to about 15 wt. % of at least one ethoxylated sulfate anionic surfactant having at least one degree of ethoxylation and/or its salt thereof, from about 1 to about 10 wt. % of at least one non-ethoxylated sulfate anionic surfactant and/or its salt thereof, from about 1 to about 5 wt. % of at least one amphoteric surfactant, from about 0.1 to about 3 wt. % of at least one water-soluble quaternary ammonium compound, and an oil-in-water emulsion having a particle size D50 of less than 350 nm.

In one embodiment, the method for manufacturing the shampoo composition comprises the steps of:

Step 1—preparation of the first phase:

(a) Add the water for the main kettle;

(b) Add the preservatives;

(c) Add the anionic surfactants;

(d) Add the silicon;

Step 2—preparation of the second phase;

(f) Add water, the cationic polymer and fatty compound;

(g) Mix well and heat during fusion;

(h) Add the amphoteric surfactant and pearlescent base and mix;

Step 3—Add the second phase into the first phase;

(i) Add the fragrance;

(j) Adjustment phase: pH and viscosity.

Method for Manufacturing a Conditioner Composition and/or A Mask Composition

The conditioner composition (B) and the mask composition (C) of the hair care system of present invention are achieved by combining the particular amounts of at least two different cationic surfactants, at least one fatty alcohol, at least two silicones and water for each of the compositions.

In one embodiment, the method for manufacturing the conditioner composition (B) and/or the mask composition (C) comprises the steps of:

(a) Adding the raw materials of the water phase in the water;
(b) Mixing and heating;
(c) Adding the silicones;
(d) Emulsification of the composition;
(e) Cooling;
(f) Adding the fragrance and the remaining additional ingredients.

EXAMPLES

The following Examples are intended to be non-restrictive and explanatory only, with the scope of the invention being defined by the claims.

The ingredient amounts in the compositions/formulas described below are expressed in % by weight, based on the total weight of the composition/formula.

Example 1—Preparation of the Silicone Emulsion of the Shampoo Composition (A) of the Hair Care System 450 g of fluid aminosilicone (copolymer of dimethylsiloxane-aminoethylaminopropylmethylsiloxane comprising trimethylsilyl end groups, having an amine number of 7.2 mg of KOH/g and a viscosity of 5,600 mPa·s at 25° C.) are transferred into a 1st vessel; 1,800 g of dimethylsiloxane comprising trimethylsilyl end groups, having a viscosity of 61,500 mPa·s at 25° C., are added, with stirring, and the stirring is maintained for 2 hours at ambient temperature.

In a separate vessel, 49 g of steareth-6 and 62 g of PEG100 stearate are mixed, and the mixture is heated to 60° C. The mixture is maintained at this temperature until a liquid mixture is obtained, then 31 g of trideceth-3 and 350 g of trideceth-10 (80% of active material) are added. The surfactant mixture has an HLB=11.25. 80 g of water and 6.2 g of glacial acetic acid are added and the stirring is continued until a creamy paste is obtained.

The content of this 2nd vessel (creamy paste) is then transferred into the 1st vessel (containing the silicones), then the mixture obtained is mixed for 30 minutes at ambient temperature (20-25° C.). The mixing steps are carried out in order to obtain a homogeneous mixture; they are carried out at ambient temperature.

79.6 g of demineralized water are added and mixing is carried out for 60 minutes.

72.7 g of demineralized water are added and mixing is carried out for 50 minutes.

197.4 g of demineralized water are added and mixing is carried out for 5 minutes.

294.3 g of demineralized water are added and mixing is carried out for 5 minutes. 180 g of demineralized water are added and mixing is carried out for 5 minutes.

180 g of demineralized water are added and mixing is carried out for 5 minutes.

197.4 g of demineralized water are added and mixing is carried out for 5 minutes.

197.4 g of demineralized water are added and mixing is carried out for 3 minutes.

228.5 g of demineralized water are added and mixing is carried out for 3 minutes.

Finally, 40.5 g of 2-phenoxyethanol (preservative) are added and mixing is carried out for 3 minutes.

An oil-in-water emulsion having a particle size D50 of 170 nm is obtained.

Examples 2 to 9—Shampoo Compositions (A)

Suitable shampoo compositions according to the state of the art are as Examples 2 to 4, and suitable shampoo compositions (A) according to the present invention are as Examples 5 to 9, as follows.

All ingredients are expressed in wt. %, relative to the total weight of the composition unless otherwise indicated:

TABLE 1

Comparison between the shampoo compositions of the state of the art and of the present invention

| FUNCTION | INGREDIENT | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Ethoxylated Sulfate Anionic Surfactant | sodium laureth sulfate | 10-10.5 | 7-7.5 | 4.6-5.6 | 7.6-8.6 | 7.6-8.6 | 7.6-8.6 | 7.6-8.6 | 7.6-8.6 |
| Non-Ethoxylated Sulfate Anionic Surfactant | sodium lauryl sulfate | — | 2.0-2.6 | 2.0-2.6 | 4.3-5.0 | 4.3-5.0 | 4.3-5.0 | 4.3-5.0 | 4.3-5.0 |
| | ammonium lauryl sulfate | — | — | — | — | — | — | — | — |
| Amphoteric Surfactant | cocamidopropyl betaine and/or coco-betaine | 1.16 | 0.3 | 2.0 | 2.8 | 2.8 | 2.8 | 2.8 | 2.9 |
| Water-Soluble Quaternary Ammonium Compound | guar hydroxypropyltrimonium chloride | 0.1-3 | 0.1-3 | 0.1-3 | 0.1-3 | 0.1-3 | 0.1-3 | 0.1-3 | 0.1-3 |
| Silicone | Dimethicone | — | 0.75 | — | — | — | — | — | — |
| | Amodimethicone* | — | — | 0.8 | — | — | — | — | — |
| | Silicone emulsion** as prepared in Example 1 (silicones + nonionic surfactants) | 2.8 | — | — | 1 | 1 | 1 | 1 | 1 |

TABLE 1-continued

| Comparison between the shampoo compositions of the state of the art and of the present invention | | | | | | | | | |
|---|---|---|---|---|---|---|---|---|---|
| FUNCTION | INGREDIENT | Ex. 2 | Ex. 3 | Ex. 4 | Ex. 5 | Ex. 6 | Ex. 7 | Ex. 8 | Ex. 9 |
| Non-Ionic surfactants | cocamide MEA trideceth-6 | 0.5-1 | 1.5-2.0 | 0.05-0.1 | 0.5-1 | 0.5-1 | 0.5-1 | 0.5-1 | 0.5-1 |
| Pearl agent | glycol distearate | 0.1-0.5 | 1.5-2.0 | 1.5-2.0 | 1-1.4 | 1-1.4 | 1-1.4 | 1-1.4 | 1-1.4 |
| Thickening agent | carbomer | 0.2 | 0.2 | 0.1 | — | — | — | — | — |
| Salt | sodium chloride | 1.2-1.5 | 1.2-1.5 | 0.0.8-1 | 0.5-1 | 0.5-1 | 0.5-1 | 0.5-1 | 2.5-2.8 |
| Additional ingredients | pH adjusters fragrance preservatives fillers pigments | ≤3.0 | ≤3.0 | ≤3.0 | ≤3.0 | ≤3.0 | ≤3.0 | ≤3.0 | ≤3.0 |
| Solvent | hexylene glycol | 0.4 | — | 0.4 | 0.5 | 0.5 | 0.5 | 0.5 | 1 |
| | Water | Q.S. | Q.S. | Q.S. | Q.S. | Q.S. | Q.S. | Q.S. | Q.S. |

*available under the tradename of XIAMETER MEM-8299 EMULSION from Dow Corning
**50% active material ("AM) of silicones - 40% AM polydialkylsiloxane and 10% AM aminosilicone

Examples 10 to 13—Conditioner Compositions (B)

Suitable conditioner compositions according to the state of the art are as Examples 10 to 12, and suitable conditioner compositions (B) of the hair care system according to the present invention are as Examples 13, as follows.

All ingredients are expressed in wt. %, relative to the total weight of the composition:

TABLE 2

| Comparison between the conditioner compositions of the state of the art and of the present invention | | | | | |
|---|---|---|---|---|---|
| FUNCTION | INGREDIENT | Ex. 10 | Ex. 11 | Ex. 12 | Ex. 13 |
| Cationic Surfactant | cetrimonium chloride | 0.01-0.05 | — | — | 0.5-1 |
| | behentrimonium chloride | 2.0-3.0 | 2.0-3.0 | 2.0-3.0 | 1-1.5 |
| Fatty Alcohol | cetearyl alcohol | 6 | 7 | 4 | 4.5 |
| Silicone | dimethicone | — | — | — | 2.0-2.5 |
| | amodimethicone | 0.5-1.0 | — | — | 0.2-0.6 |
| | bis-cetearyl amodimethicone | — | — | 1.5-2.0 | — |
| Non-silicone oil | Mineral oil | — | 2.0-4.0 | 2.0-4.0 | — |
| Additional ingredients | pH adjusters fragrance preservatives fillers pigments | ≤3.0 | ≤3.0 | ≤3.0 | ≤3.0 |
| Solvent | glycerin | — | 0.5 | — | 2 |
| | isopropyl alcohol | 0.54 | 0.54 | 0.45 | — |
| | water | Q.S. | Q.S. | Q.S. | Q.S. |

Example 14—Mask Composition (C)

Suitable mask compositions (C) of the hair care system according to the present invention are as Example 14, as follows.

The ingredients are expressed in wt. %, relative to the total weight of the composition:

TABLE 3

| Mask compositions according to the present invention | | |
|---|---|---|
| FUNCTION | INGREDIENT | Ex. 14 |
| Cationic Surfactant | cetrimonium chloride | 0.5-1.0 |
| | behentrimonium chloride | 1.5-2.0 |
| Fatty Alcohol | cetearyl alcohol | 5.5 |
| Silicone | imethicone | 0.2-0.4 |
| | modimethicone | 0.5-0.8 |
| Additional ingredients | pH adjusters fragrance preservatives fillers pigments | ≤3.0 |
| Solvent | glycerin | 2.5 |
| | water | Q.S. |

Example 15—Proof of Performance

In order to measure the performance of the hair care system of the present invention in light of the prior art, a blind product test was conducted with about 100 volunteers per group, all women between the ages of 18 and 65, having medium to long hair length, mixed hair type and thickness, who use shampoo and conditioner at least twice per week.

At least one group of volunteers, blindly, used the hair care system of the present invention, comprising the shampoo composition (A) and the conditioner composition (B), and at least one group of volunteers used, blindly, a hair care treatment according to the prior art.

In order to perform such tests, the volunteers used either the hair care treatment of the present invention or the hair care treatment of the prior art for 15 days of trial, with 2 visits face-to-face, in their homes.

After the trial period, the volunteers participated in a data collection, interviewer assisted with tablet, and filled a questionnaire (55 minutes total).

After the comparison of the volunteers' results, it was demonstrated that the hair care system according to the present invention is superior in overall liking, resulting in improved discipline, detangling, softness and cleanness, repair and texture satisfaction of the treated hair, when compared to the prior art.

Example 16—Instrumental Tests

Test 1—Breakage by Brushing

In the breakage by brushing test, bleached Caucasian Hair tresses were submitted to the application of the hair care system of the present invention, as follows:

Shampoo: the shampoo composition (A) of the hair care system was applied and rubbed in the tress for 60 seconds. Then, the tress was rinsed for 30 seconds and the excess of water was removed.

Conditioner: the conditioner composition (B) of the hair care system was applied and rubbed for 60 seconds. The composition was left on the hair for 2 minutes, then rinsed for 30 seconds, removing the excess water.

The broken fibers were counted after 1 and 20 cycles of products applications and successive brushings with a brushing machine.

The same methodology was performed with a hair care treatment of the prior art, and the results were later compared.

The hair care system of the present invention leads to a lower number of broken fibers, significantly better than the state-of-the-art.

FIG. 1 shows the results obtained from an instrumental test for evaluating hair breakage in terms of number of broken fibers using a brushing machine.

Test 2—Visual Volume and Frizz

The purpose of this study was to assess reduction in the Frizz and Volume Effect of hair tresses submitted to cosmetic treatments by means of image analysis.

In the study, tresses of wavy Caucasian hair were submitted to the hair care treatment of the present invention, as follows:

Shampoo: the shampoo composition (A) of the hair care system was applied and rubbed for 60 seconds. Then, the tress was rinsed for 30 seconds and the excess water of water was removed.

Conditioner: the conditioner composition (B) of the hair care system was applied and rubbed for 60 seconds. The composition was left on the hair for 2 minutes, then rinsed for 30 seconds, removing the excess water.

After the application of the products, the tresses were dried for 24 hours in a controlled environment at 85±5% relative humidity and 22±2° C. (initial condition). Then, the tresses were kept in environment at 85±5% relative humidity and 22±2° C., during 24 hours.

The tresses were photographed in the initial and final condition.

The same methodology was performed with a hair care treatment of the prior art, and the results were later compared.

Figure 2:
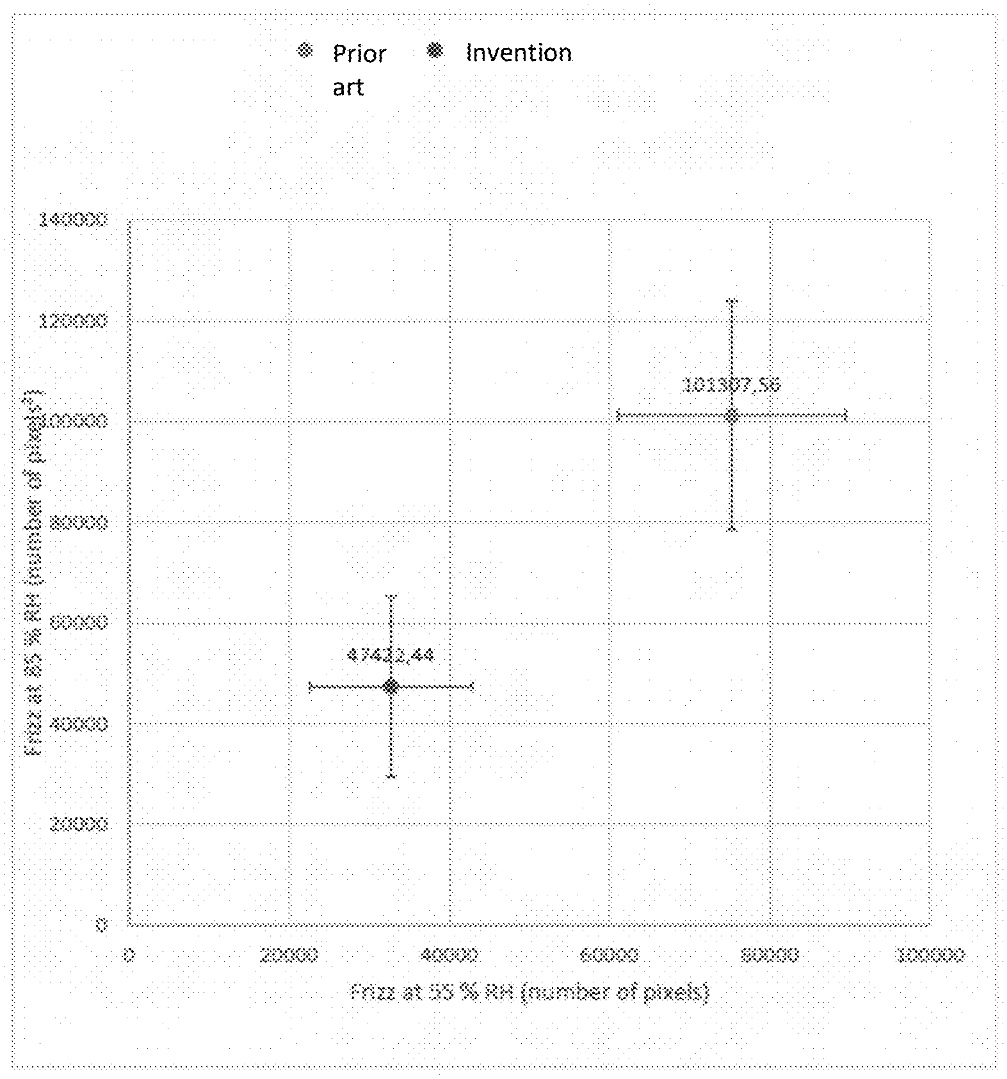
FIGS. 2 (*a*) to 2 (*b*) show, respectively, the results of the visual volume evaluation and of the visual frizz evaluation of the instrumental tests to evaluate visual volume and frizz.
Figure 2:
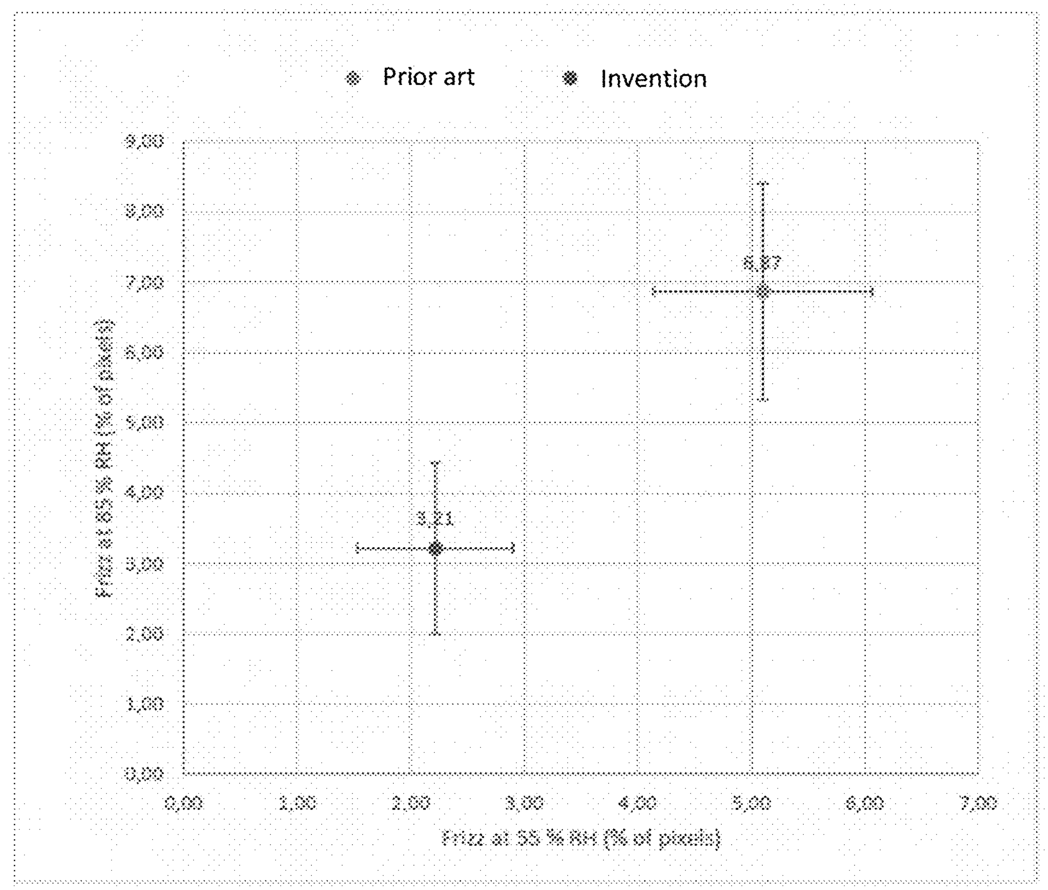

FIGS. 2 (*a*) to 2 (*b*) show, respectively, the results of the visual volume evaluation and of the visual frizz evaluation.

In the visual volume evaluation (FIG. 2 (*a*)), both in >55% RH and >85% RH, the hair care system of the present invention presented significant less hair volume and lower frizz compared to the prior art.

In the visual frizz evaluation (FIG. 2 (*b*)), both in >55% RH and >85% RH, the hair care system of the present invention presented significant lower frizz compared to the prior art.

The invention claimed is:

1. A hair care system comprising:

(A) a shampoo composition, comprising:

(a) from 5 to 15 wt. % of at least one ethoxylated sulfate anionic surfactant having at least one degree of ethoxylation and/or its salt thereof;

(b) from 1 to 10 wt. % of at least one non-ethoxylated sulfate anionic surfactant and/or its salt thereof;

(c) from 1 to 5 wt. % of at least one amphoteric surfactant;

(d) from 0.1 to 3 wt. % of at least one water-soluble quaternary ammonium compound;

(e) an oil-in-water emulsion having a particle size D50 of less than 350 nm, and comprising:

a silicone mixture comprising:

(i) a polydialkylsiloxane comprising trialkylsilyl end groups, having a viscosity at 25° C. ranging from 40,000 to 70,000 mPa·s; and (ii) an aminosilicone having a viscosity at 25° C. ranging from 1,000 to 15,000 mPa·s and an amine number ranging from 2 to 10 mg of KOH per gram of aminosilicone; and wherein the weight ratio of the polydialkylsiloxane to the aminosilicone ranges from about 5:1 to about 1:1;

a surfactant mixture comprising one or more non-ionic surfactants, said mixture having an HLB ranging from 10 to 16, and water;

wherein the oil-in-water emulsion is present in the shampoo composition (A) in a total amount ranging from about 0.1% to about 10% by weight;

all weights being based on the total weight of the shampoo composition, and (B) a conditioner composition, comprising:

(a) from 0.5 to 2 wt. % of each of at least two different cationic surfactants, in a total amount of from 1 to 4 wt. % of cationic surfactant;

(b) from 3 to 5 wt. % of at least one fatty alcohol;

(c) from 2.2 to 3.1 wt. % of at least two silicones, wherein the first silicone is a polydialkylsiloxane, which is present at a range of 2.0 to 2.5 wt. % based on the total weight of the conditioner composition, and wherein the second silicone is an aminosilicone, which is present at a range of 0.2 to 0.6 wt. % based on the total weight of the conditioner composition;

(d) water;

all weights being based on the total weight of the conditioner composition.

2. The system according to claim 1, wherein the amount of the at least one ethoxylated sulfate anionic surfactant (a) of the shampoo composition (A) ranges from 7 to 11 wt. % based on the total weight of the shampoo composition.

3. The system according to claim 1, wherein the at least one ethoxylated sulfate anionic surfactant (a) having at least one degree of ethoxylation is selected from alkyl ether sulfates, their salts thereof, and mixtures thereof, including those having the formula:

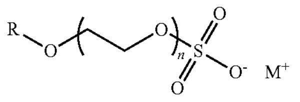

wherein:

R is an alkyl or alkenyl having from 6 to 24 (preferably, 8 to 18, more preferably, 12 to 18) carbon atoms;

n is a number having an average value of greater than at least 0.5, preferably between 1 and 4, such as from between 1 and 3 or such as from between 2 and 3; and M is a solubilizing cation such as alkali metal ions such as sodium or potassium, ammonium ions, substituted ammonium ions, alkanolammonium ions such as monoethanolammonium or triethanolammonium ions.

4. The system according to claim 1, wherein the amount of the at least one non-ethoxylated sulfate anionic surfactant (b) of the shampoo composition (A) ranges from 2 to 8 wt. % based on the total weight of the shampoo composition.

5. The system according to claim 1, wherein the amount of the at least one amphoteric surfactant (c) of the shampoo composition (A) ranges from 1.5 to 4 wt. % based on the total weight of the shampoo composition.

6. The system according to claim 1, wherein the at least one amphoteric surfactant (c) of the shampoo composition (A) is selected from betaines, alkyl amphoacetates, alkyl amphoproprionates, salts thereof, or a mixture thereof.

7. The system according to claim 6, wherein the betaines are selected from alkyl betaines, alkyl amidopropyl betaines, alkyl sulfobetaines (=sultaines), or mixtures thereof.

8. The system according to claim 6, wherein the at least one amphoteric surfactant (c) are selected from cocamidopropyl betaine, coco-betaine, or mixtures thereof.

9. The system according to claim 1, wherein the amount of the at least one water-soluble quaternary ammonium compound (d) of the shampoo composition (A) is present at an amount from 0.1 to 0.3 wt. % based on the total weight of the shampoo composition.

10. The system according to claim 1, wherein the at least one water-soluble quaternary ammonium compound (d) of the shampoo composition (A) is derived from guar gum.

11. The system according to claim 10, wherein the at least one water-soluble quaternary ammonium compound (d) is selected from guar hydroxypropyltrimonium chloride, hydroxypropyl guar hydroxypropyl trimonium chloride, or a mixture thereof.

12. The system according to claim 1, wherein the polydialkylsiloxane is selected from dimethicones.

13. The system according to claim 1, wherein the aminosilicone is selected from amodimethicones.

14. The system according to claim 1, further comprising:
(C) a mask composition comprising:
(a) at least two different cationic surfactants, in a total amount of from 2.0 to 3.0 wt. % of cationic surfactant;
(b) from 4 to 8 wt. % of at least one fatty alcohol;
(c) from 3.0 to 6.0 wt. % of at least two silicones; and
(d) water;
all weights being based on the total weight of the mask composition.

15. A method for treating hair with the hair care system of claim 1 comprising:
(a) washing the hair with the shampoo composition (A);
(b) rinsing the hair;
(c) applying the conditioner composition (B);
(d) rinsing the hair;
(e) optionally, applying a mask composition (C) comprising:
(a) at least two different cationic surfactants, in a total amount of from 2.0 to 3.0 wt. % of cationic surfactant;
(b) from 4 to 8 wt. % of at least one fatty alcohol;
(c) from 3.0 to 6.0 wt. % of at least two silicones; and
(d) water;
all weights being based on the total weight of the mask composition.

16. The system according to claim 1, wherein the polydialkylsiloxane comprising trialkylsilyl end groups, having a viscosity at 25° C. ranging from 51,000 to 70,000 mPa·s.

17. The system according to claim 1, wherein the oil-in-water emulsion is present in the shampoo composition (A) in a total amount ranging from about 0.2% to about 8% by weight; the silicone mixture is present in a total amount ranging from 40% to 60% by weight relative to the total weight of the emulsion; the polydialkylsiloxane comprising trialkylsilyl end groups is present in a total amount ranging from 35% to 45% by weight relative to the total weight of the emulsion; the aminosilicone(s) is present in a total amount ranging from 5% to 15% by weight relative to the total weight of the emulsion; the surfactant mixture is present in a total amount ranging from 5% to 15% by weight relative to the total weight of the emulsion; and the water is present in a total amount ranging from 25% to 50% by weight of the emulsion.

18. The system according to claim 14, wherein the at least two different cationic surfactants of the mask composition comprise 0.5-1.0 wt. % of cetrimonium chloride and 1.5-2.0 wt. % of behentrimonium chloride.

* * * * *